US010368759B2

(12) United States Patent
Yu et al.

(10) Patent No.: US 10,368,759 B2
(45) Date of Patent: Aug. 6, 2019

(54) METHOD AND SYSTEM FOR DETERMINING INTRACRANIAL PRESSURE

(71) Applicant: Lions Eye Institute Limited, Nedlands, Western Australia (AU)

(72) Inventors: Dao-Yi Yu, Nedlands (AU); William Morgan, Nedlands (AU)

(73) Assignee: LIONS EYE INSTITUTE LIMITED, Nedlands, Western Australia (AU)

(*) Notice: Subject to any disclaimer, the term of this patent is extended or adjusted under 35 U.S.C. 154(b) by 226 days.

(21) Appl. No.: 15/122,519

(22) PCT Filed: Mar. 6, 2015

(86) PCT No.: PCT/AU2015/000127
§ 371 (c)(1),
(2) Date: Aug. 30, 2016

(87) PCT Pub. No.: WO2015/131236
PCT Pub. Date: Sep. 11, 2015

(65) Prior Publication Data
US 2017/0065193 A1    Mar. 9, 2017

(30) Foreign Application Priority Data
Mar. 7, 2014 (AU) .............................. 2014900767

(51) Int. Cl.
*A61B 5/03* (2006.01)
*A61B 5/00* (2006.01)
(Continued)

(52) U.S. Cl.
CPC ................ *A61B 5/031* (2013.01); *A61B 3/12* (2013.01); *A61B 3/1233* (2013.01); *A61B 3/145* (2013.01);
(Continued)

(58) Field of Classification Search
CPC ....... A61B 5/031; A61B 3/12; A61B 5/02216; A61B 3/16; A61B 3/1233; A61B 5/03
See application file for complete search history.

(56) References Cited

U.S. PATENT DOCUMENTS

| 5,671,737 | A | 9/1997 | Hirosi |
| 2004/0230124 | A1 | 11/2004 | Querfurth |
| 2013/0211285 | A1 | 8/2013 | Fuller et al. |

FOREIGN PATENT DOCUMENTS

EP    2 567 656    3/2013
(Continued)

OTHER PUBLICATIONS

International Search Report dated May 21, 2015 out of priority Application No. PCT/AU2015/000127 (10 pages).
Written Opinion of the International Searching Authority dated May 21, 2015 out of priority Application No. PCT/AU2015/000127 (9 pages).
Notification of Transmittal of the International Preliminary Report on Patentability out of priority Application No. PCT/AU2015/000127 (35 pages).
(Continued)

*Primary Examiner* — May A Abouelela
*Assistant Examiner* — David Joseph Fernandez-Fidalgo
(74) *Attorney, Agent, or Firm* — Brinks Gilson & Lione; John C. Freeman

(57) ABSTRACT

A method and apparatus for determining intracranial pressure includes a contact lens; a camera for making a plurality of images of at least one eye of a subject; one or more force transducers for controllably applying a force to the eye via the contact lens; a support system for supporting the camera, the contact lens and the one or more force transducers against the eye; and a computing device for controlling the force applied to the eye by the force transducers and stabilizing the force by negative feedback.

14 Claims, 9 Drawing Sheets

(51) Int. Cl.
*A61B 3/12* (2006.01)
*A61B 3/14* (2006.01)
*A61B 3/16* (2006.01)
*A61B 5/022* (2006.01)

(52) U.S. Cl.
CPC .............. *A61B 3/16* (2013.01); *A61B 5/0077* (2013.01); *A61B 5/02216* (2013.01); *A61B 5/6821* (2013.01); *A61B 5/6885* (2013.01); *A61B 5/7278* (2013.01)

(56) References Cited

FOREIGN PATENT DOCUMENTS

| WO | WO 98/09564 | 3/1998 |
| WO | WO 99/52426 | 10/1999 |
| WO | WO 99/65387 | 12/1999 |
| WO | WO 00/25662 | 5/2000 |
| WO | WO 2006/091811 | 8/2006 |

OTHER PUBLICATIONS

Article, Entenmann et al., Contact Lens Tonometry—Application in Humans, Investigative Ophthalmology & Visual Science, Nov. 1997, vol. 38, No. 12, pp. 2447-2451.

Article, Hoffmann et al., Intraocular Pressure and Ocular Phase Amplitude Using Dynamic Contour Tonometry and Contact Lens Tonometry, BMC Opthalmology, Mar. 23, 2004, vol. 4, No. 1, the entire document.

Article, Morgan et al., Retinal Vein Pulsation is in Phase with Intracranial Pressure and not Intraocular Pressure, Investigative Ophthalmology & Visual Science, Jul. 2012, vol. 53, No. 8, pp. 4676-4681.

Article, Morgan et al., Optimizing the Calibration and Interpretation of Dynamic Ocular Force Measurements, Graefes Archive for Clinical and Experimental Ophthalmology, 2010, vol. 248, No. 3, pp. 401-407.

Article, Kain et al., New Observations Concerning the Nature of Central Retinal Vein Pulsation, British Journal of Ophthalmology, 2010, vol. 94, pp. 854-857.

European Search report from EP15758954.0, dated Mar. 19, 2018, 8 pages.

__US 10,368,759 B2__

METHOD AND SYSTEM FOR DETERMINING INTRACRANIAL PRESSURE

This application claims priority to International Application No. PCT/AU2015/000127filed Mar. 6, 2015 and to Australian Application No. 2014900767 filed Mar. 7, 2014; the entire contents of each are incorporated herein by reference.

RELATED APPLICATION

This application is based on and claims the benefit of the filing and priority dates of Australian patent application No. 2014900767 filed 7 Mar. 2014, the content of which as filed is incorporated herein by reference in its entirety.

FIELD OF THE INVENTION

The present invention relates to a method and system for determining intracranial pressure, of particular but by no means exclusive application to making accurate, non-invasive measurements of intracranial pressure, to predicting absolute intracranial pressure and changes in intracranial pressure non-invasively, and to estimating resistance and capacitance of retinal veins.

BACKGROUND OF THE INVENTION

The measurement and monitoring of intracranial pressure (ICP) for instantaneous (absolute) pressures as well as changes in pressure among patients with head injury, stroke oedema, idiopathic intracranial hypertension, hydrocephalus, papilloedema, acute intracranial haemorrhage and other conditions, provides necessary, and often vital information upon which medical and surgical treatment can be based. More recently, ICP has been found to be related to Glaucoma.

ICP is equivalent to intracranial cerebrospinal fluid (CSF) pressure and the latter appears to be equivalent to optic nerve subarachnoid space pressure when the pressure is greater than 0 mmHg. This subarachnoid space, containing CSF, surrounds the optic nerve up to the back of the eye. The classical theory of venous pulsation requires the presence of a gradient down the vein between the intraocular and retrolaminar optic nerve compartments so that the venous pressure is equivalent to intraocular pressure at its exit point on the disc surface. Intraocular pressure oscillations induced by the cardiac cycle leading to an intraocular pressure peak during systole were thought to cause a compressive force to act upon the venous walls at the exit and hence for intermittent collapse to occur in time with cardiac systole. The existence of a significant 7-13 mmHg pressure difference between the intra-ocular venous pulsation pressure and intracranial pressure has been a well-documented requirement for venous pulsation in healthy, normal dog, primate and humans. This pressure difference is thought to be due to central retinal vein resistance (narrowing), lamina cribrosa and other factors, and varies between individuals, becoming a major source of error when using ophthalmodynamometric methods to estimate ICP.

Currently, invasive techniques are used to measure ICP despite the many shortcomings of such practices. Continuous ICP measurement devices to monitor these conditions require a surgeon to drill a hole through the skull to implant transducers within brain tissue or to locate fluid connected tubes into the central brain ventricles. Intermittent measures can be obtained by needle puncture of the lumbar dura by spinal tap, to measure the cerebrospinal fluid (CSF) pressure. (CSF pressure and ICP are known to be equivalent so the terms are used interchangeably.)

Such procedures carry the risk of brain haemorrhage (up to 6%), malfunction, brain herniation and/or infection (up to 27%) and, furthermore, are expensive. Invasive ICP measuring devices comprise external ventricular drains (EVD) coupled to transducers and tissue microtransducers (e.g. Camino, Codman, Raumedic) all inserted through skull burr holes. Relevant diseases (described above) involve disorders of elevated ICP, but other disorders such as glaucoma, normal tension hydrocephalus and ventriculo-peritoneal shunt overdrain require ICP monitoring and are partly caused by low ICP.

Other non-invasive approaches have been proposed to estimate ICP, including using the combination or retinal arterial flow velocities and venous pulsation pressure (Cerepress), tympanic membrane displacement in the ear, ultrasonic detection of cranial pulsations, transcranial Doppler (TCD) ultrasonography of the middle cerebral artery, optic nerve sheath diameter and CT or MRI assessment of CSF volume. However, none of these has been shown to be sufficiently accurate at high ICP and none gives any useful measurements at low ICP.

Furthermore, existing non-invasive technologies have poor accuracy. For example, the tympanic membrane displacement method is based on acoustic stapedial reflex that, in theory, can measure intracranial pressure indirectly by measuring displacement of the eardrum since ICP is transmitted from the CSF to the perilymphatic fluid of the scala tympana in the labyrinth. However, this method has drawbacks due to the indirect nature of the measurement, poor accuracy and the necessity of having a patent, unobstructed cochlear aqueduct.

TCD ultrasonography provides a real-time spectral waveform of blood flow velocity in intracranial vessels. However, with many head injury patients, flow velocities in unilateral intracranial vessels may either increase or decrease due to vasospasms, loss of normal cerebrovascular auto-regulation or other reasons. Furthermore, other physiologic variables, such as cardiac output, pulse rate, hematocrit, positive end expiratory pressure (if ventilated) and carbon dioxide tension can alter TCD parameters. Accordingly, TCD ultrasonography cannot predict absolute ICP from instantaneous readings and, as a result, only trends can be inferred and, in any event, is difficult owing to the anatomic variability of the cerebral vasculature.

An ophthalmodynamometric method for estimating ICP was first described in 1925 by Baurmann. More recent techniques combine ophthalmodynamometry with reflectance oximetry of the retina or ultrasound measurement of blood flow in the central retinal artery (see US 2004/0230124), or automate the method by adding a camera and image processing software for detecting venous pulsations from a sequence of images of the eye fundus (see US 2006/0206037). However, the accuracy of ophthalmodynamometry combined with reflectance oximetry or central retinal artery flow appears little different from ophthalmodynamometry alone.

Classically, an ophthalmodynamometer has been used to apply force (ODF) on the eye, and elevate intraocular pressure (IOP), while an observer views the central retinal vein and notes the force when retinal vein pulsation just begins. The induced IOP is then calculated from the baseline IOP and ODF and termed the venous pulsation pressure (VPP). VPP determination is very subjective due to varying abilities of observers to detect the threshold at which veins pulsate. This adds one element of error to the measurement. Any automated method using blood column analysis suffers from the variation in human retinal vein anatomy, with there being markedly varying shapes and sizes of the retinal veins. Some more recent techniques rely upon detecting changes within the central retinal vein wall, but this is a small venous segment with great variation between individuals so both human judgement of its pulsation or machine judgement of size variation using threshold change detection is prone to wide variation and hence inaccuracy.

SUMMARY OF THE INVENTION

According to a first broad aspect, the present invention provides a method for determining intracranial pressure (ICP) of a subject, the method comprising:
producing a plurality of intraocular pressure (IOP) values within an eye of the subject by applying force to the eye
imaging retinal vein and arterial pulsation of the eye of the subject by obtaining a plurality of images of the retina of the eye at the plurality of IOP values over at least one cardiac cycle (and desirably over three or more cardiac cycles);
determining blood column density data by analysing the images;
determining from the blood column density data amplitudes of blood column depth pulsation as a function of intraocular pressure (IOP).

In an embodiment, the method includes producing the plurality of intraocular pressure (IOP) values within the eye by applying force to the eye with an ophthalmodynamometer force (ODF) device.

In another embodiment, the method includes determining the ICP using: i) the amplitudes of blood column depth pulsation; ii) the amplitudes of blood column depth pulsation and the retinal vein discharge rate; or iii) the amplitudes of blood column depth pulsation and the central retinal vein discharge rate.

In one embodiment, the method includes determining the ICP with nested multivariate algorithms. In an embodiment, the IOP is a function of the ODF value. In a further embodiment, the determining of blood column depth pulsation as a function of IOP employs curve fitting to and averaging of the blood column density data In another embodiment, the method includes determining from the blood column density data a retinal vein charge (inflow) rate. In still another embodiment, the method includes determining the ICP using the amplitudes of blood column depth pulsation and blood column depth pulsation timing information. In one example, the timing information includes a timing difference. The timing difference may be between time points of venous and arterial pulse maximum values and/or between time points of venous and arterial pulse minimum values. Alternatively, the timing difference may be between venous and arterial pulse maximum points and/or minimum points for both upper and lower hemiveins.

In one embodiment, the ODF device is a video ophthalmodynamometer force device having a camera (such as a video camera) attached to a contact lens within a force transducer ophthalmodynamometer and adapted to perform the imaging and the measuring of VPP.

The method may include measuring a baseline intraocular pressure (IOP) of the subject with an intraocular pressure measurement device (such as a tonometer), measuring venous pulsation pressure (VPP) of the subject using an ophthalmodynamometer force (ODF) device and determining venous pulsation pressure (VPP) of the subject using the ODF and the baseline IOP thus measured.

The method may further comprise measuring VPP of the other eye of the subject with the ODF device, and imaging retinal vein and arterial pulsation in the other eye at a plurality of ODF values and over at least one cardiac cycle (and desirably over three or more cardiac cycles).

Recently, the present inventors have found that the ICP pressure waveform dominates the phase and timing of pulsation in the central retinal vein. ICP systole, IOP systole and venous systole (dilation) occur in phase. The time delay between IOP (and retinal arterial systole) and retinal venous systole is altered by retinal venous changes including intrinsic resistance and external compression. Additionally, the shape of the retinal venous pulsation curve over the cardiac cycle is affected by these retinal venous changes. These factors can be measured according to the present invention and allow the correction to be made for retinal venous narrowing and capacitance changes caused by intrinsic venous disease or external compression. Venous intrinsic disease is known to occur in glaucoma and venous occlusive disorders. External compression occurs commonly in papilloedema and other diseases. All of these factors cause known large errors in non-invasive measurements of ICP using ophthalmodynamometric related techniques. The present invention allows at least some of these sources of error to be circumvented or reduced.

In one embodiment, the imaging comprises making at least one video recording.

The method may include determining one or more of an absolute ICP, a change in ICP, ICP waveform, retinal venous resistance, arterial resistance and arterial compliance.

In one embodiment, the method includes measuring a baseline intraocular pressure and a baseline blood pressure, for use in improving accuracy.

In one embodiment, the method includes determining pulse (such as with a pulse oximeter) and using a pulse timing signal for cardiac cycle timing.

The method may include inducing different levels of IOP, such as ranging in steps from normal (approximately 10 mmHg) to approximately 60 mmHg, using the ODF device. This may be done by controlling the ODF device to apply a stepwise force and thereby induce an IOP rise above baseline from 0 mmHg to a corresponding plurality of levels (that may include a level of approximately 50 mmHg), such as in steps from 0 to 150 g force (or, in another embodiment, 0 to 120 g force) to the eye of a subject. Alternatively, the different levels of IOP may be applied with diminishing values, or otherwise. The method may include using a calibration coefficient (e.g. 0.32 mmHg/g force for Ocudyn (trade mark) device, and other coefficients for other contact lens sizes) to calculate induced IOP. This may be optimized for a particular subject by comparing diastolic blood pressure to diastolic retinal arterial ophthalmodynamometric force.

According to a second broad aspect, the present invention provides an apparatus for determining intracranial pressure, comprising: a contact lens; a camera (such as a video camera) for making a plurality of images of at least one eye of a subject; one or more force transducers (such as in the form of a force ring transducer) for controllably applying a force to the eye via the contact lens; a support system for supporting the camera, the contact lens and the one or more force transducers against the eye; and a computing device for controlling the force applied to the eye by the force transducers and stabilizing the force by negative feedback.

Thus, the apparatus can be used to perform video dynamometry. The force transducers and contact lens constitute a ophthalmodynamometer that is stabilised by the force actuators.

The apparatus may include an intraocular pressure measurement device (such as a tonometer) for measuring a baseline intraocular pressure (IOP) of the subject.

The apparatus may include a light source for illuminating at least a portion of the eye.

In one embodiment, the apparatus is configured to facilitate measurements over a stepwise force range from 0 to 150 grams force (i.e. 0 to approximately 1.47 N) when held by an operator.

In one embodiment, the apparatus is configured to determine venous and arterial blood column size and density by analysing images collected with the camera of at least one optic disc and immediate surrounds.

Spontaneous venous pulsation is unlikely to occur when the ICP is greater than 20 cmH2O (15 mmHg) and the IOP required to induce venous pulsation (venous pulsation pressure—VPP) increases as ICP rises. It is now appreciated that the VPP is also affected by venous resistance so, according to the present invention, it is possible to estimate venous resistance using curve fitting and hence remove (or minimize) venous resistance as a confounding factor in predicting ICP. Also, according to the present invention VPP may be more objectively quantified, by observing densitometry fluctuations in time with cardiac cycle.

According to a third broad aspect, the present invention provides computer software that, when executed by one or more processes, controls a computing device to perform a method for determining intracranial pressure (ICP) of a subject, the method comprising:

receiving images of retinal vein and arterial pulsation of an eye of the subject collected at a plurality of intraocular pressure (IOP) values over at least one cardiac cycle, the plurality of IOP values produced by application of force to the eye;

determining blood column density data by analysing the images; and determining from the blood column density data amplitudes of blood column depth pulsation as a function of intraocular pressure (IOP).

The method may include producing the plurality of IOP values by controlling an ophthalmodynamometer force (ODF) device to apply force to the eye. The method may further comprise determining the ICP using: i) the amplitudes of blood column depth pulsation; ii) the vessel pulsation timing data; or iii) using the vessel pulsation slope (charge and discharge) data.

The method may comprise controlling an imaging device (such as an ODF device) to image the retinal vein and arterial pulsation of the eye of the subject.

This aspect also provides a computer readable medium comprising the computer software product described above.

It should be noted that any of the various features of each of the above aspects of the invention, and of the various features of the embodiments described below, can be combined as suitable and desired.

BRIEF DESCRIPTION OF THE DRAWINGS

In order that the invention may be more clearly ascertained, embodiments will now be described, by way of example, with reference to the accompanying drawing, in which.

DETAILED DESCRIPTION

Figure 1:
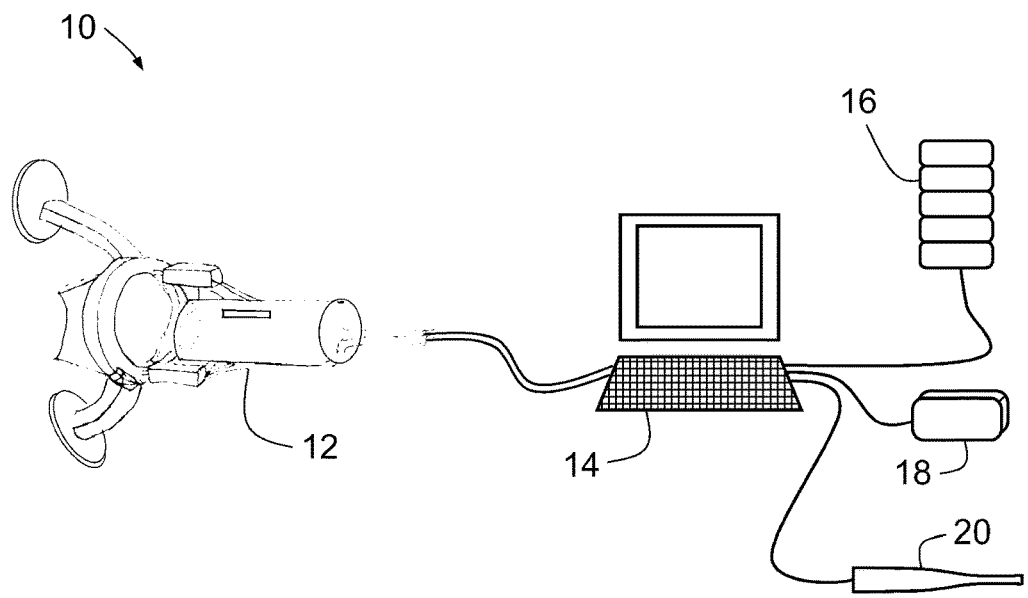
FIG. 1 is a schematic view of a system for determining intracranial pressure according to an embodiment of the present invention.

FIG. 1 is a schematic view of a system 10 for determining intracranial pressure according to an embodiment of the present invention. System 10 includes an ophthalmodynamometer force measuring apparatus in the form of ODF device 12, and a computing device in the form of computer 14, in data communication with ODF device 12.

Computer 14 has a processor, a memory and an interface (which includes a data input, an output and a display). Computer 14 is adapted to allow the inputting of information about the subject, such as blood pressure and haemoglobin concentration, and can display video images collected by ODF device 12 of the optic disk blood vessels and allow the manual selection of venous and arterial segments if required. The operator can adjust the ODF force settings of ODF device 12 using computer 14.

System 10 also includes a blood pressure meter in the form of digital sphygmomanometer 16, for measuring the blood pressure of a subject, a pulse oximeter 18 for monitoring of the saturation of the haemoglobin of the subject, and an intraocular pressure measurement device in the form of a tonometer 20 for determining a baseline value of the intraocular pressure of the subject (such as a Tono-pen™ or Icare™ tonometer), all in data communication with computer 14.

Pulse oximeter 18 is a standard pulse oximeter with signal (beep) generated towards the peak of the systole. The output signals of pulse oximeter 18 are used by computer 14 to form the start timing for video sequence recording, as discussed below.

Figure 2:
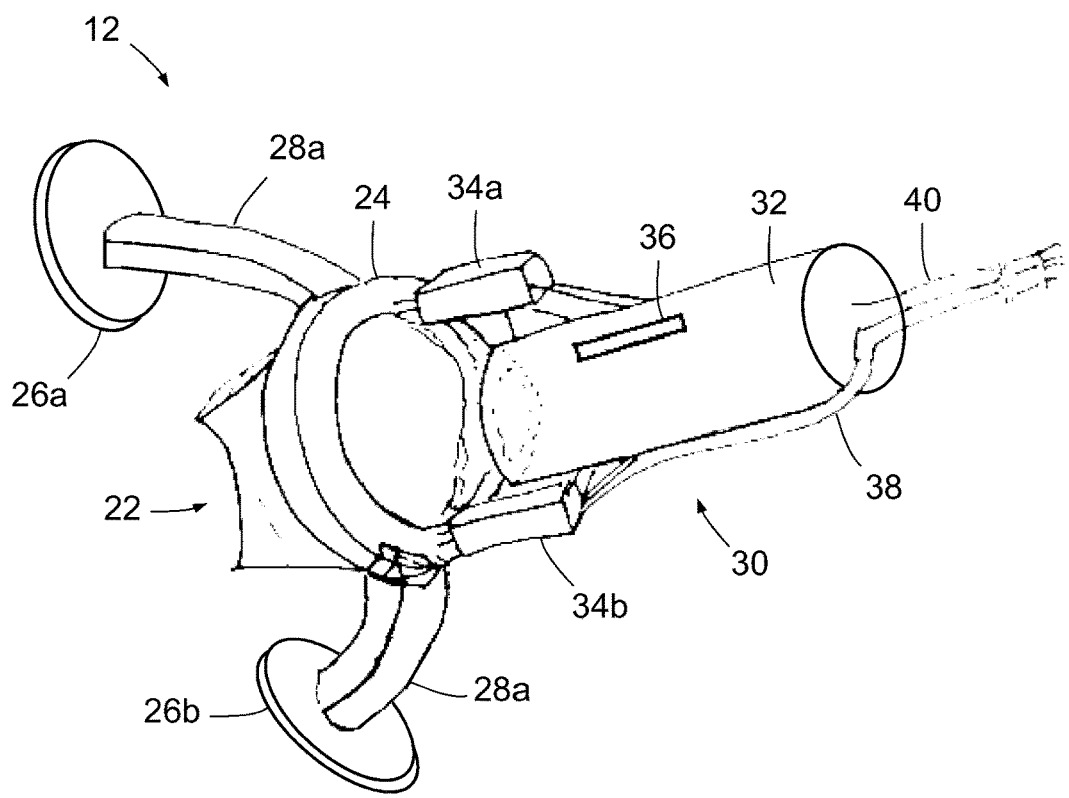
FIG. 2 is a schematic view of the ophthalmodynamometer force (ODF) device of the system of FIG. 1.

ODF device 12 is shown schematically in greater detail in FIG. 2. ODF device 12 comprises a contact lens 22 and a ring force transducer 24, within which is set the contact lens 22. In other embodiments, one or more a force or pressure transducers may be used to hold the contact lens. In this embodiment, ring force transducer 24 comprises a Cooper Instruments (trade mark) multiple strain-gauge ring force transducer connected to a modified Wheatstone bridge signal detector, and a signal conditioning module for digital signal collection, amplification, conditioning and digitization, for transmission to computer 14. Computer 14 stores the output of ring force transducer 24 coordinated with a pulse timing signal obtained from pulse oximeter 18 (discussed below).

ODF device 12 includes three facial stabilizers (of which two, 26a, 26b, are visible in the view of FIG. 2), for supporting ODF device 12 on three contact areas of a subject's face (possibly with the assistance of an operator), namely, the bridge of the nose, the brow and a cheek, and three corresponding flexible arms (of which two, 28a, 28b, are visible in the view of FIG. 2). The stabilizers 26a, 26b are connected to ring force transducer 24 by the flexible arms 28a, 28b, and thereby spaced generally equidistantly around ring force transducer 24. The flexibility of flexible arms 28a, 28b allows the stabilizers 26a, 26b to be adjustable so that the contact lens 22 can be positioned against the eye of the subject. Optionally, additional facial stabilizers and corresponding arms may be employed.

ODF device 12 also includes a video-dynamometer 30 comprising a camera in the form of video camera 32, three force actuators (of which two, 34a, 34b, are visible in the view of FIG. 2), and a light source (not shown) to illuminate the retina with white light. Video camera 32 is mounted to ring force transducer 24 with the force actuators 34a, 34b. In this embodiment, video camera 32 has a standard 3-chip CCD for receiving red, green and blue colour channels, and a focus adjustment control dial 36 for adjusting the depth of the focal plane of the video camera. The output of video camera 32 is transmitted to computer 14, which makes video sequence recordings initiated in synchrony with signals from pulse oximeter 18 (discussed below).

Video-dynamometer 30 has a small display (not shown) that displays to the operator the current view of video camera 32.

White light from the light source traversing a separate optical path, but in parallel to, return light reflected from the retina and propagating to the CCD of the video camera 32. The light source is controlled and varied to optimize colour contrast across the green and red colour channels.

Force actuators 34a, 34b can impart a force to video camera 32, and hence to the eye of the subject, and comprise servo-electromagnets to impart the force under the control of computer 14 using a negative feedback loop with data outputted by the force transducers. In use, computer 14 typically controls the force transducers to successively apply force to the eye at values of 0, 10, 20, 30, 45, 60, 90 and 120 grams force, and force measurements from the force transducer 34a, 34b being continuously analysed by computer 14 and fed back to the force actuators 34a, 34b using a programmed negative feedback system to stabilise the force applied to the eye.

ODF device 12 includes control and data cables 38 and 40, for communication between computer 14 and—respectively—ring force transducer 24 and the video-dynamometer 30.

Figure 3:
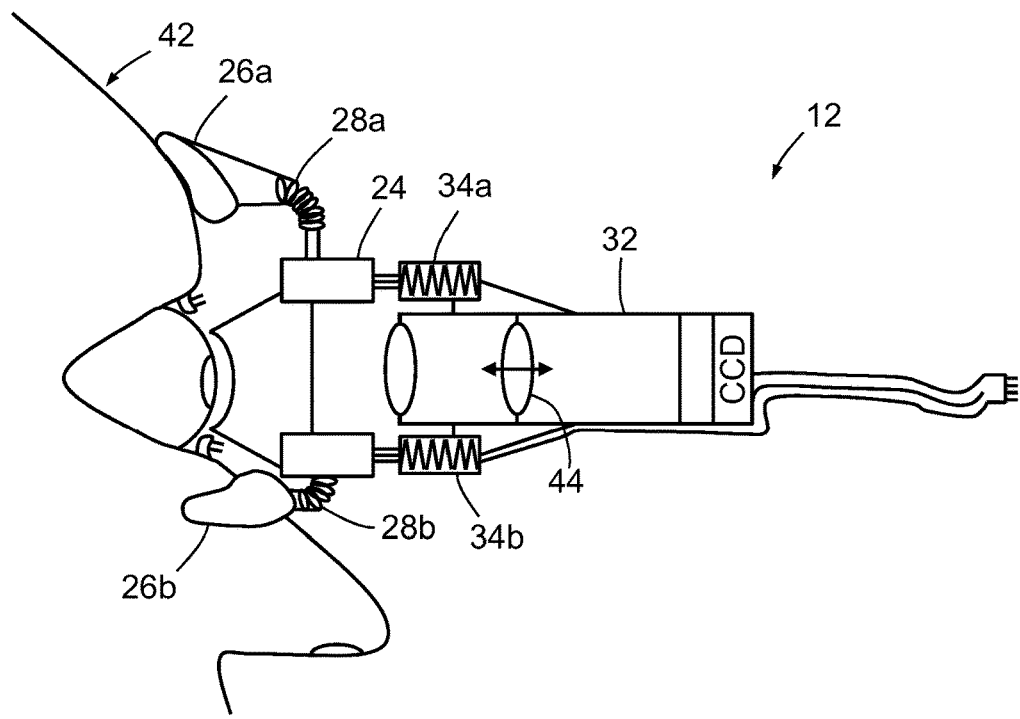
FIG. 3 is a cross-sectional schematic view of the ODF device of FIG. 2 in use, supported on the face of a subject.

FIG. 3 is a cross-sectional schematic view of ODF device 12 in use, supported on the face 42 of a subject. As is apparent in this view, video camera 32 includes a plurality of optical elements, at least one optical element 44 of which is adjustable along the optical axis to effect the adjustment in the depth of the focal plane described above.

Figure 4:
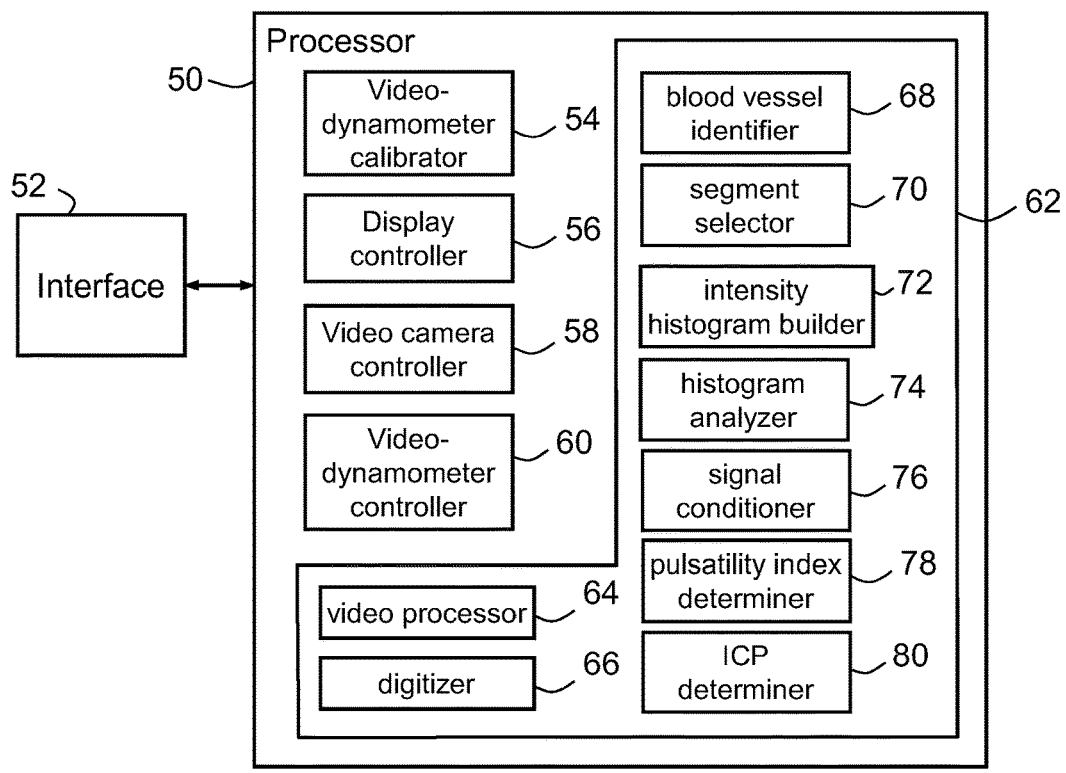
FIG. 4 is a schematic view of the processor and interface of the computer of the system of FIG. 1.

FIG. 4 is a schematic view of the processor 50 and interface 52 of computer 14. The more important components of processor 50 are shown in this figure, though some components—as will be understood to be present by the skilled person—have been omitted for clarity.

Thus, processor 50 includes a video-dynamometer calibrator 54 that uses blood pressure measurements from digital sphygmomanometer and general calibration coefficients to calibrate video-dynamometer 30, a display controller 56 to control the display (to display, for example, the current view of video camera 32), video recording controller 58 for controlling video camera 32, a video-dynamometer controller 60 for controlling video-dynamometer 30 (including to control the force applied by video-dynamometer 30 to the eye and to stabilize that force by negative feedback), and a data processing module (for data conditioning and analysis) 62.

Data processing module 62 includes a video processor 64 for storing video signal received from video camera 32 as video sequence recordings comprising separate images aligned to the baseline image using the output signal of pulse oximeter 18 as a timing signal, a digitizer 66 for digitizing the video signal if it is in analogue form, a blood vessel identifier 68, which identifies hemiretinal vein and tributaries using colour channel separation, a segment selector 70 for selecting separate vessel segments close to the central optic disc entry point, an intensity histogram builder 72 for creating for each frame within each segment sequence a histogram comprising the number of pixels containing light over the range of brightness intensities, a histogram analyzer 74 for analysing these histograms (as is described in detail below), and a signal conditioner 76 for performing signal averaging, noise reduction, comparison to mean values, along and curve fitting.

Data processing module 62 also includes a pulsatility index determiner 78 for determining pulsatility indices, and a ICP determiner 80, which compares pulsatility curve fits to standard curves, exclude poor datasets, identifies the minimum ODF at which threshold intensity units per pixel amplitude occurred, calculates intracranial pressure, and estimates ICP waveform, central retinal vein resistance and retinal arterial compliance.

The functions of each of the components of data processing module 62 are described in greater detail below.

System 10 is used to determine intracranial pressure as follows. As is described below, system 10—when in operation—collects data from retinal hemiveins and central retinal artery branches from both optic discs at varying intraocular pressures (the variation induced by varying ODF), collects baseline intraocular pressure, systolic and diastolic blood pressure at eye level, and times the cardiac cycle to generate video frame collection start points. The video frame collection and controlled intraocular pressure manipulation are performed using video-dynamometer 30.

The subject is preferably examined while seated, but can be examined in any posture including supine (such as on an ICU bed or if unconscious following trauma). System 10 can be used with an undilated pupil in most circumstances, but dilation (by standard techniques) of very small pupils may be desirable for optimal data collection.

Figure 5A:
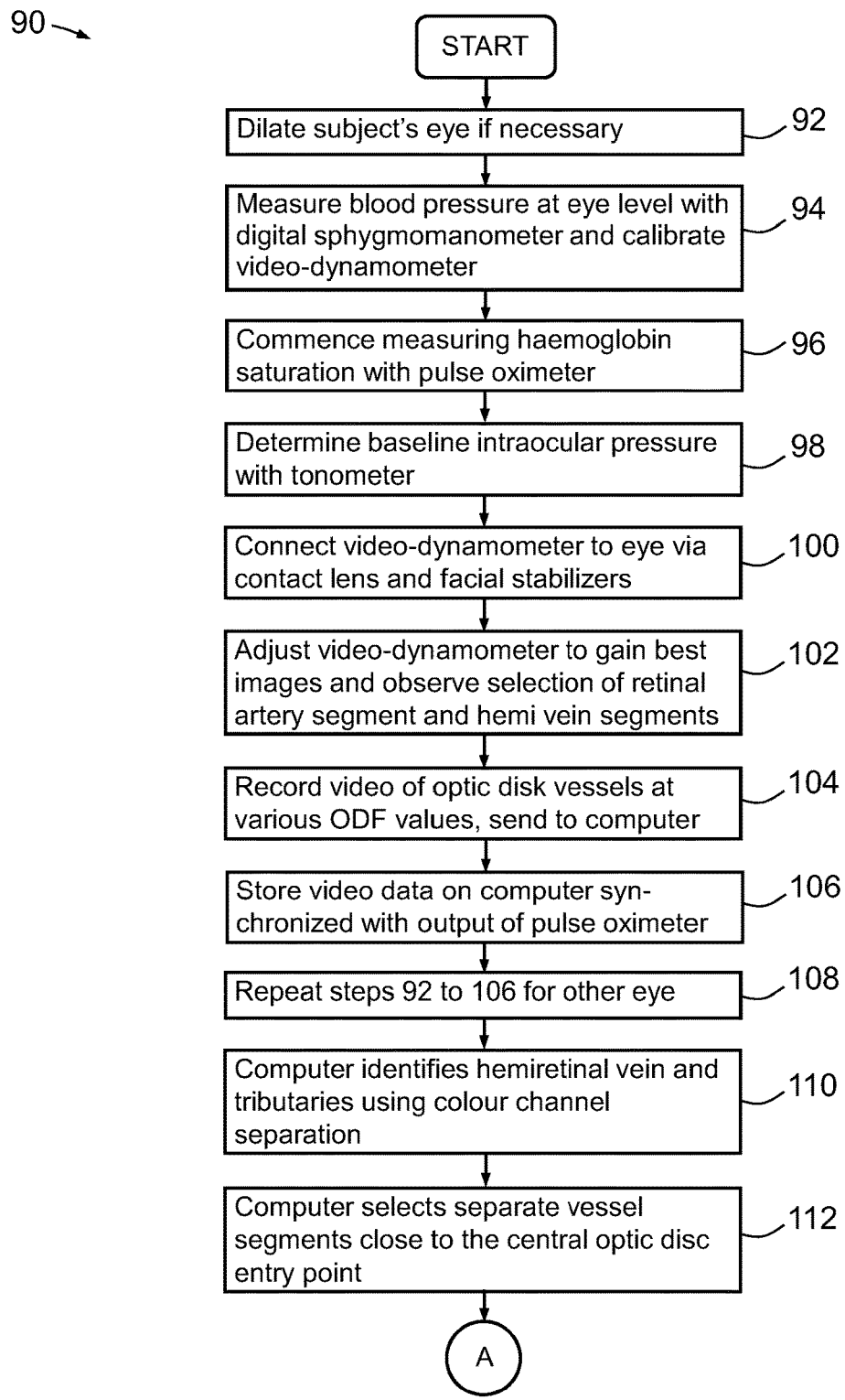
FIGS. 5A and 5B are a flow diagram of the method of use of the system of FIG. 1.
Figure 5B:
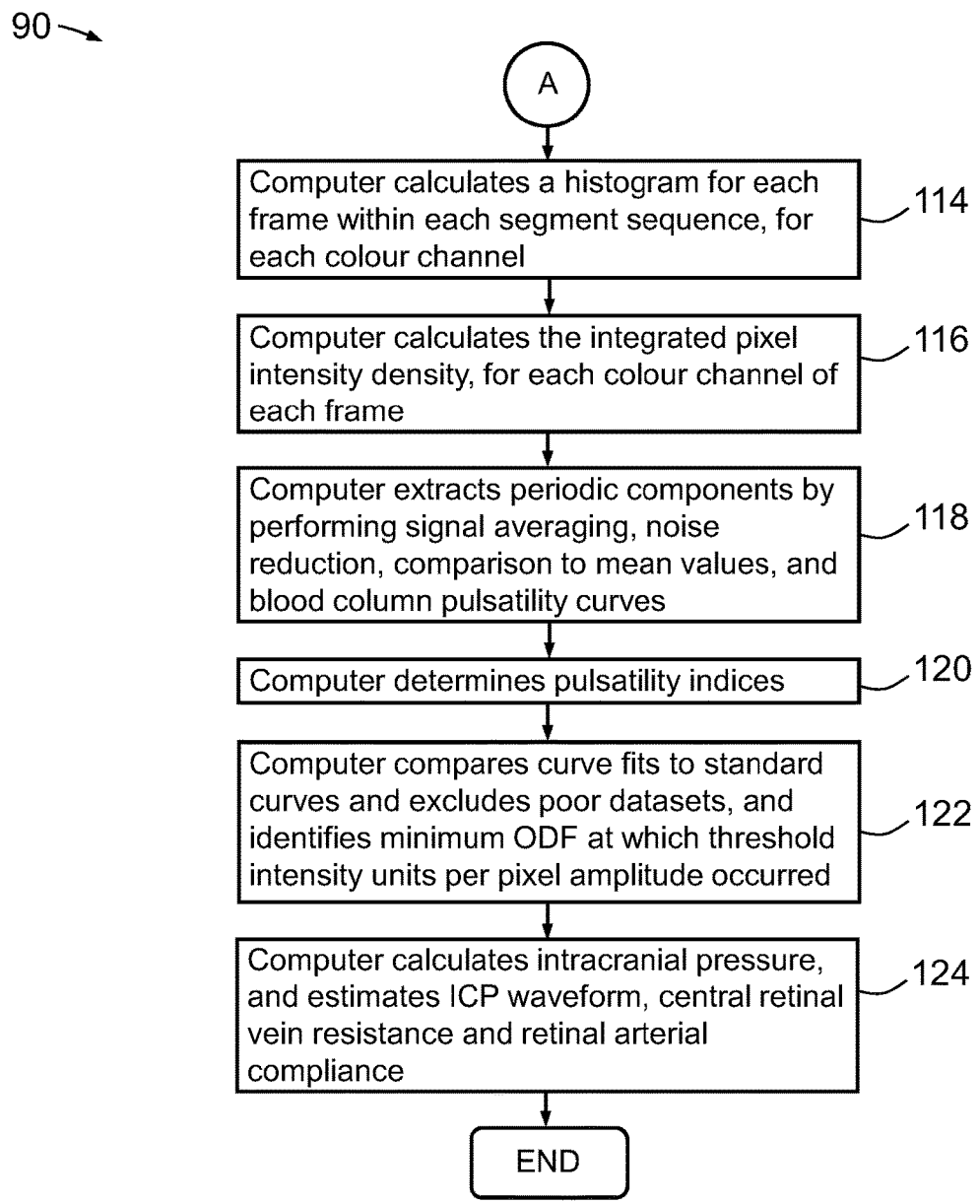

Thus, FIGS. 5A and 5B are a flow diagram 90 of the method of use of system 10. At step 92, the subject's pupil is dilated if desired or necessary. At step 94, blood pressure is measured at eye level with digital sphygmomanometer 16 and transmitted to computer 14, which uses the results to then fine-tune the calibration of the video-dynamometer 30. This is done using the blood pressure measurements of digital sphygmomanometer 16.

The systolic and diastolic blood pressure, measured while the cuff of digital sphygmomanometer 16 is held at eye level, are used by computer 14 to calculate an estimate of ophthalmic artery blood pressure. Computer 14 uses this value, as well as general calibration coefficients, to calibrate video-dynamometer 30 so that, subsequently, computer 14 can convert applied force and baseline IOP into the induced IOP at which images of retinal vessels are collected. This allows a more accurate VPP to be calculated. This calibration is conducted by computer 14 controlling video-dynamometer 30 to apply sufficient force to the eye to reach central retina artery diastolic pressures (equivalent to ophthalmic artery pressure) and provide a calibration point using the blood pressure measured—as described above—using digital sphygmomanometer 16.

At step 96 pulse oximeter 18 commences measuring and transmitting to computer 14 haemoglobin saturation values.

At step 98, tonometer 20 is used to determine a baseline intraocular pressure of the subject and to send the result to computer 14.

At step 100, the video-dynamometer 30 is connected to an eye of the subject with contact lens 22 and facial stabilizers 26a, 26b. Typically, an anaesthetic drop is applied to the eye in order to facilitate contact lens application. Contact lens application also typically requires that a small amount of contact gel be placed on contact lens 22 before its application to the surface of the eye, to improve optical transmission and subject comfort.

At step 102, video-dynamometer 30—with light source in operation—is adjusted to optimize image quality and to observe a selection of retinal artery segment and hemi vein segments. The operator holds video-dynamometer 30 on the subject's eye and adjusts the position of video-dynamometer 30 in order to centre the optic disc and its blood vessels, and can view the result to obtain feedback on the small display of video-dynamometer 30 (or, indeed, on the display of computer 14); the operator uses focus adjustment control dial 36 to optimize focussing.

At step 104, a video recording is made of the eye at successive ODF values of 0, 10, 20, 30, 45, 60, 90 and 120 grams force, with each video recording then transmitted to computer 14. In this embodiment, each video recording comprises 25 frames per second, but higher frame rates may be employed to increase the quantity of data by collecting more data in each cardiac cycle. At each force step, computer 14 determines the force actually being applied from measurements made by ring force transducer 24 and—using a negative feedback loop—adjusts the signal to force actuators 34a, 34b whilst monitoring the force with ring force transducer 24 and thereby stabilizes the force being applied to the eye for the duration of the video recording.

The collection of the video recordings is initiated by the operator, but computer 14 then controls the collection of the recordings, including controlling the force applied by video-dynamometer 30, and allows sufficient time at each force value for vessel acclimatisation (typically 3 seconds) followed by collection of a video recording across three cardiac cycles for each ODF values and hence each intraocular pressure step.

At step 106, which is performed essentially simultaneously with step 104, computer 14 stores the video recordings or data as video sequence recordings comprising the storage of each frame of each video recording as a separate image aligned to the baseline image using transposition image alignment techniques and a timing signal—to facilitate temporal alignment—comprising essentially the output signal of pulse oximeter 18. If the video recordings are in analogue form, computer 14 digitizes each recording before storing it.

At step 108, steps 92 to 106 are repeated for the subject's other eye.

At step 110, computer 14 commences analysis of the video recordings, by identifying hemiretinal vein and tributaries using colour channel separation. Vessels with a higher red component are identified as arteries, while those with higher green and blue components identified as veins. The operator may optionally override the computer's categorization.

At step 112, computer 14 selects separate vessel segments close to the central optic disc entry point, each segment comprising at least 400 pixels in area to maximise data collection and minimise noise. The operator may, again, override the computer's vessel segmentation selection if desired. Thus, in this step upper hemivein, lower hemivein (or tributaries) and central retinal artery (or branch) are segmented from the aligned three cardiac cycle sequence.

At step 114, for each colour channel, computer 14 determines an intensity histogram for each frame within each segment sequence comprising the number of pixels containing light over the range of brightness intensities from 0 to 255. It will be appreciated that in this embodiment the colour channels are (and generally will be) red, green and blue, but other colour channels may be employed in other embodiments.

At step 116, computer 14 analyzes the resulting histograms, determining—for each frame—the integrated pixel intensity density as the sum of the number of pixels times their particular intensity. This involves calculating a non-weighted mean of histogram (when CCD gamma is 1) or a weighted mean according to light intensity/pixel intensity (camera gamma) and haemoglobin colorimetry function.

It should be noted that the results to this point may be based on a single cardiac cycle, but are more desirably collated from data collected over plural cardiac cycles, and typically at least three (or possibly four or five) cardiac cycles.

At step 118, computer 14 performs signal averaging, noise reduction and comparison to mean values, along with curve fitting, to extract periodic components and calculate pulsatility indices for each vessel at each ODF value. The major feature changing in each segment is the vessel blood column, so variations in image integrated densitometry reflect change in vessel blood column width and depth (via optical density). This is calculated by the above described integrated densitometry technique, with which computer 14 estimates blood column size change in selected vascular windows and compares frames to determine the change in blood column over the cardiac cycle and determine blood column pulsatility curves.

Figure 8A:
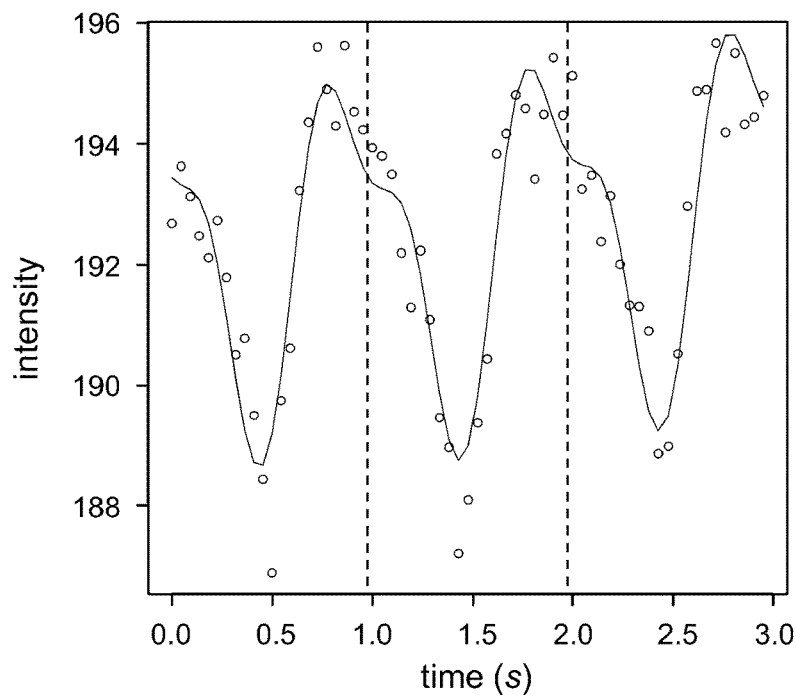
FIG. 8A is a curve fitted over three cardiac cycles of data using a Fourier two frequency model on lower hemivein data, wherein the dichrotic notch (the hump in the downphase) influence of CSF pressure can be seen detected.

From these results, computer 14—at step 120—uses curve fitting algorithms, computer 14 to determine the following pulsatility indices:
1) the down slope of venous emptying (related to venous resistance);
   i) The slope of vein collapse is greater when the resistance is lower because the blood column can drain into the optic nerve more rapidly;
   ii) A greater gradient (more negative because it is going down) will be associated with a greater ICP owing to the lower resistance separating intraocular venous compartment from the CSF compartment;
2) the up slope of venous filling (related to venous compliance) relates to retinal blood flow and can be used to balance downslope;
3) the amplitude of venous column pulsation (used to modulate VPP calculation);
   i) The greater the amplitude indicates that current ODF is proportionally greater than minimum ODF required for pulsation to just occur (that at vein pulsation pressure);
   ii) Also, if vein pulsation is spontaneous and minimum ODF is nominally zero, then true minimum ODF would be more negative (less than baseline IOP) with a greater amplitude;
   iii) Consequently, a higher amplitude indicates a somewhat lower ICP;
4) the timing difference between venous peak dilation and arterial peak dilation (related to venous resistance);
   i) A greater timing delay is expected with greater resistance;
   ii) A greater timing delay will be associated with a lower ICP owing to the higher resistance separating intraocular venous compartment from the CSF compartment;
5) the timing difference between venous peak dilation and IOP maxima (related to venous resistance);
   i) A greater timing delay is expected with greater resistance;
   ii) A greater timing delay will be associated with a lower ICP due to the higher resistance separating intraocular venous compartment from the CSF compartment;
6) dichrotic notch (hump in the down-phase) and other features of ICP waveform from the curve of FIG. 8A shape derived from Fourier component curve fit. This also allows the measurement of slope at any point along the curve particularly at set time points (e.g. 0.1 to 0.3 s after maxima and minima, to standardize the charge and discharge indices), using the first differential and also the calculation of maximum slope. The dichrotic notch can be detected using the second order differential and its timing is useful to compare between arterial and venous vessel, with shorter time differences indicating reduced venous resistance.
7) the pulsatility of the central retinal artery (and tributary) arteriolar wall, including characteristics such as compliance, amplitude, flexibility of the vessel wall, pulse transmission (from the aorta) and dichrotic notch transmission; these characteristics may be used to estimate the degree of arteriolarsclerosis in ocular and brain tissue, which is relevant to microvascular stroke risk, as they are likely to be reduced in atherosclerotic arterial disease; and
8) Central retinal and hemiretinal vein resistance, which is relevant to risk of retinal venous occlusion.

In performing this analysis to determine the pulsatilty indices, computer 14 employs curve fitting routines including linear regression analysis, exponential functions set within a sine curve (see the "capacitance model", described below) and Fourier analysis with two-(or more) frequency function; computer 14 determines in the course of this analysis minima and maxima intensity (which is related to blood column volume) and timing, amplitudes, slopes and inflection points (by double differential).

In this embodiment, computer 14 optionally uses haemoglobin concentration (from a separate blood test), in these calculations to improve the accuracy of the blood column estimations and slope calculations. The haemoglobin concentration affects the optical density of the blood (it is the major determinant). Theoretically, including haemoglobin concentration in our models may improve their accuracy.

Computer 14 thus performs this analysis at the different ODF values and in both eyes using a nested (and weighted) multivariate analysis. The weighted analysis calculates a weighted mean for multiple interrelated measurements (at different ODF, left and right eyes and upper and lower venous segments all within the same subject) with the weighting partially determined by curve fit quality and also the fitted model values for interrelated factors. For example, in this embodiment the prediction formula uses 80% of the lower hemivein values and 20% of the upper hemivein values (cf. FIG. 9) with a modification based upon curve fit quality.

In this analysis, computer 14 also employs IOP, minimum ODF of upper and lower hemiveins (required for their pulsation), the ODF force to pressure calibration and an adjustment for variation in illumination light intensity. Strictly speaking, $VPP=IOP+k\times ODF$, where ODF is the minimum ODF required for visible venous pulsations to be seen, which depends upon the observer and anatomy of the veins. By quantifying the pulsations, this technique allows an objective measure of when vessel pulsation occurs (above a threshold amplitude of densitometry change over the cardiac cycle) and the identification of the corresponding ODF. In this embodiment, k (the calibration constant) is 0.32, but this will vary with the contact lens surface area of ODF device 12.) Computer 14 determines absolute downslopes (i.e. the rate of decrease in blood column—including maximal slope and at set timepoints) at varying ODF and their relationship to varying ODF, absolute amplitudes at varying ODF and their relationship to varying ODF, absolute timing differences (artery to vein maxima and minima) at varying ODF and their relationship to varying ODF, and absolute upslopes (rate of rise of blood column—maximal slope and at set timepoints) at varying ODF and their relationship to varying ODF.

Each cardiac cycle sequence is assumed to start and finish at approximately equal values. Any significant trend away from these level start and finish values is adjusted by computer 14 using a simple linear weighting technique so that the periodic component is emphasized. The linear weighting technique employs two methods. The first assumes that the start of each cardiac cycle occurs at the same densitometry value, and so any difference is recorded, then this value is divided by the interval frame count (e.g. 1 cycle per second would have a frame count of 25) to get a change per frame value (v). The count value c (e.g. 3rd frame after initial frame=3) after the initial frame is multiplied by the above frame value ($=c\times v$) and added to the densitometry value. This has the effect of removing any apparent tilt in the curve.

The second method uses the Fourier analysis results and extracts the periodic (frequency) component only, effectively removing any D.C. shift induced by a varying illumination (usually produced by subject eye movement).

At step 122, computer 14 compares pulsatility curve fits to standard curves and exclude poor datasets, and identifies the minimum ODF at which threshold intensity units per pixel amplitude occurred. At step 124, computer 14 calculates intracranial pressure, and estimates ICP waveform, central retinal vein resistance and retinal arterial compliance.

The "capacitance model" employed by computer 14 uses the relationship:

$$ICP = k_0 + k_1 \cdot IOP + k_2 \cdot ODFu + k_3 \cdot Uvsxn + k_4 \cdot Uvamp + k_5 \cdot AUVmax$$

wherein, in this embodiment:
- $k_0 = -4.6$;
- $k_1 = 0.25$;
- $k_2 = 0.57$;
- $k_3 = -36.6$;
- $k_4 = -3.6$;
- $k_5 = -0.66$
- ODFu=ODF in upper vein (though computer 14 can use the lower hemivein depending upon the data quality assessment, that is, how closely it fits the typical curve, and both upper and lower hemi-venous ODF values can be used with weighting applied according to the quality of the data fit);
- Uvsxn=venous down-phase slope (either or both upper or lower hemivein data can be used);
- Uvamp=venous densitometry amplitude (either or both upper or lower data can be used); and
- AUVmax=timing difference (arterial–venous) between venous and arterial pulse maximal points, for both upper and lower hemiveins.

The coefficients (k), though treated as constants, are expected to be refined with new data and analysis. Computer 14 performs multiple calculations for each ODF setting and each eye and determines an average (weighted according to data quality).

Computer 14 may also use the arterial pulsation data to estimate retinal artery diastolic closing force or pressure. As part of the segmentation of images performed by computer 14, computer 14 may also use an area of optic disc containing no detectable blood vessels as a background in order to measure the background illumination and its variation. This is useful for several reasons. For example, an estimate of background illumination and its variation allows computer 14 to estimate the variation in illumination light intensity, which can be used to alter the simple linear weighting method referred to above, and—additionally—to estimate the degree of arterial collapse, as the arterial background reflectance becomes somewhat similar to a non-vessel background when arteries are maximally collapsed and the blood column is eliminated from one particular segment. Creating an arterial pulsation in which baseline to blood column density decreases to 50% of background intensity is approximately equivalent to total arterial collapse, so this effect can be used by computer 14 to estimate the arterial collapse force. Computer 14 can also compare the diastolic blood pressure taken initially to this value and make adjustments in the force to intraocular pressure calibration accordingly, thereby allowing computer 14 to fine-tune the calibration and hence calculation of intracranial pressure.

System 10, as described above, comprises a separate sphygmomanometer 16, pulse oximeter 18, tonometer 20, video-dynamometer 30, connected to computer 14. However, it is envisaged that embodiments of the invention will include an integrated device for performing two or more of the functions of all these components of system 10. Indeed, a system is envisaged according to the invention adapted to perform the control and analysis functions of computer 14 and pulse oximeter 18 (and in some embodiments of tonometer 20) within a video-dynamometer device.

EXAMPLE

System 10 was tested, with human subjects, with the following exemplary results. The subjects were individuals undergoing ICP monitoring in a neurosurgery department high-dependency unit with either an external ventricular drain (EVD) or an intraparenchymal strain gauge intracranial pressure monitor (ICPM). Video recordings of the subjects' optic disks and peripapillary retina were obtained with an ophthalmodynamometer at varying ODF settings. At each setting, recordings of three cardiac cycles were taken and digitized for further analysis in the manner described.

Figure 6:
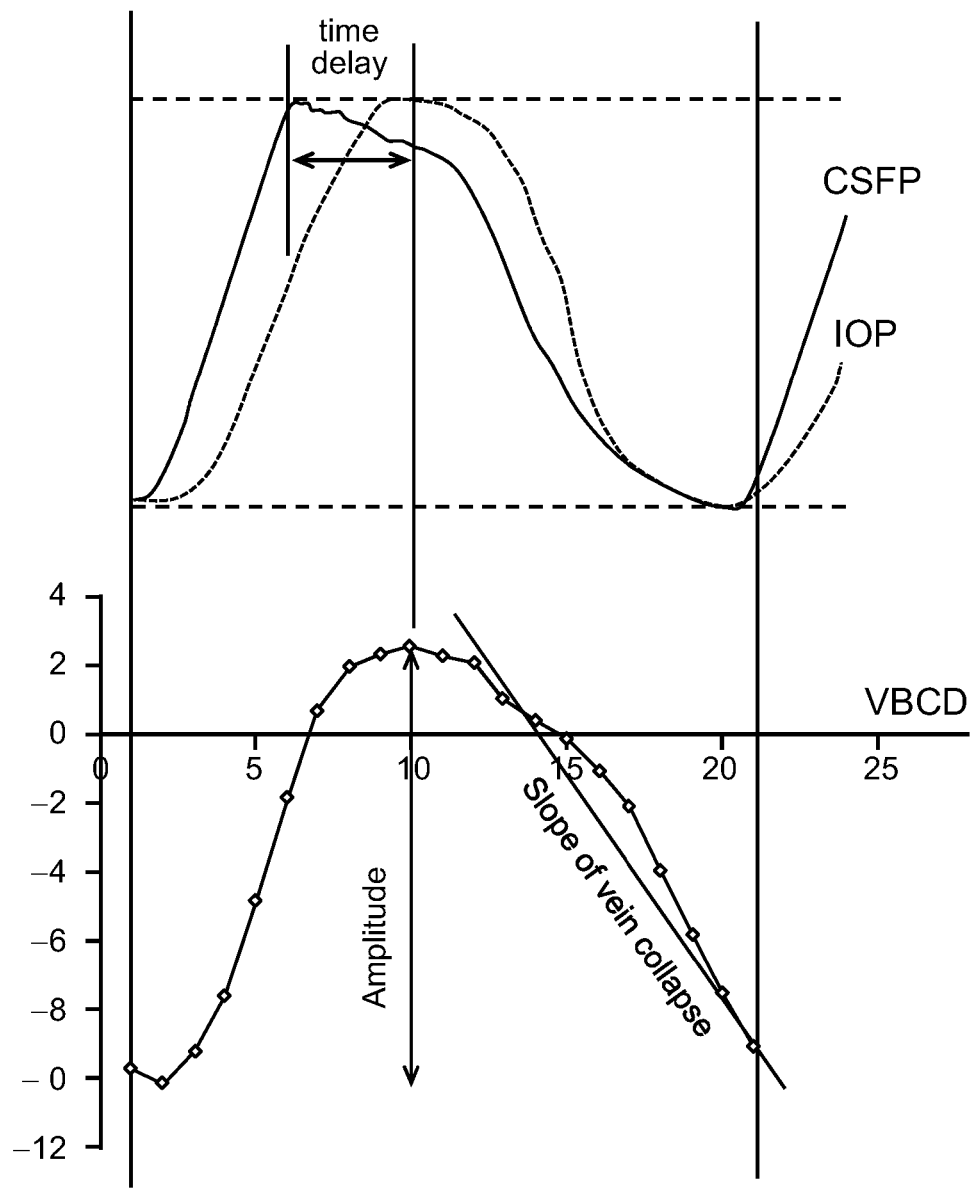
FIG. 6 presents a plot of a typical retinal venous blood column dimension over the cardiac cycle (lower register) and a plot of ICP (CSFP) and IOP (upper register)

FIG. 6 presents a plot of a typical retinal Venous Blood Column Dimension (VBCD) over the cardiac cycle (lower register) shown—with aligned timing—with a plot of ICP (CSFP) and IOP (upper register). The vertical scales may be regarded as being in arbitrary units, though in fact they represent integrated intensity×frequency values subtracted from initial values, and relate to blood column size (density and width). FIG. 6 may make it appear that computer 14 has employed the timing difference between IOP and Vein pulsation peaks, but in fact the timing difference between the Arterial and venous peaks was employed.

Figure 7A:
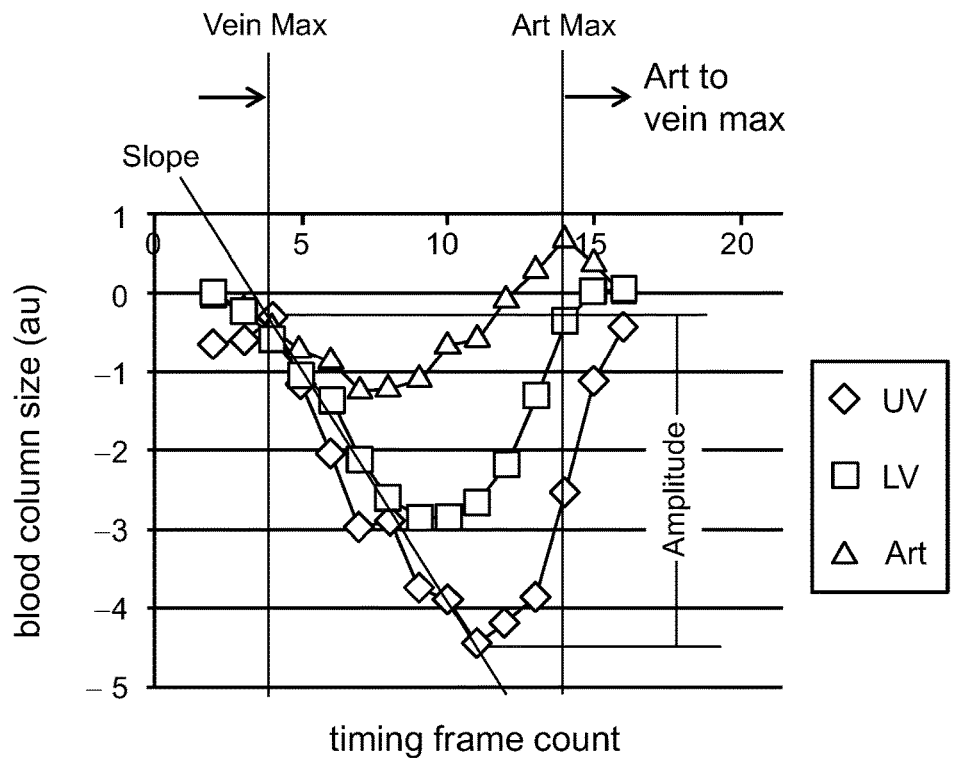
FIGS. 7A and 7B are plots of typical vessel blood column curves over a cardiac cycle.
Figure 7B:
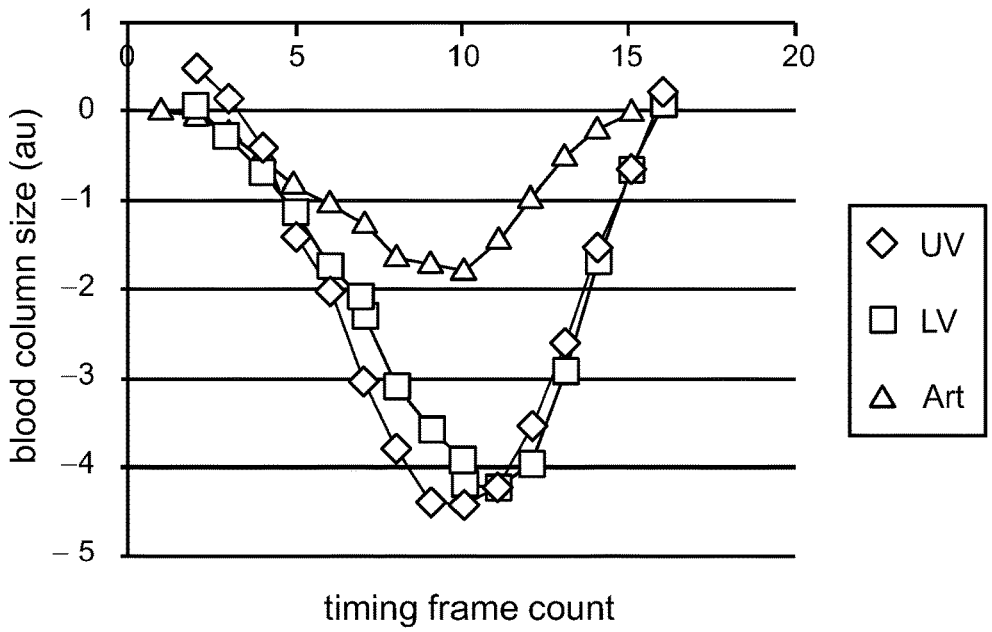
Figure 7C:
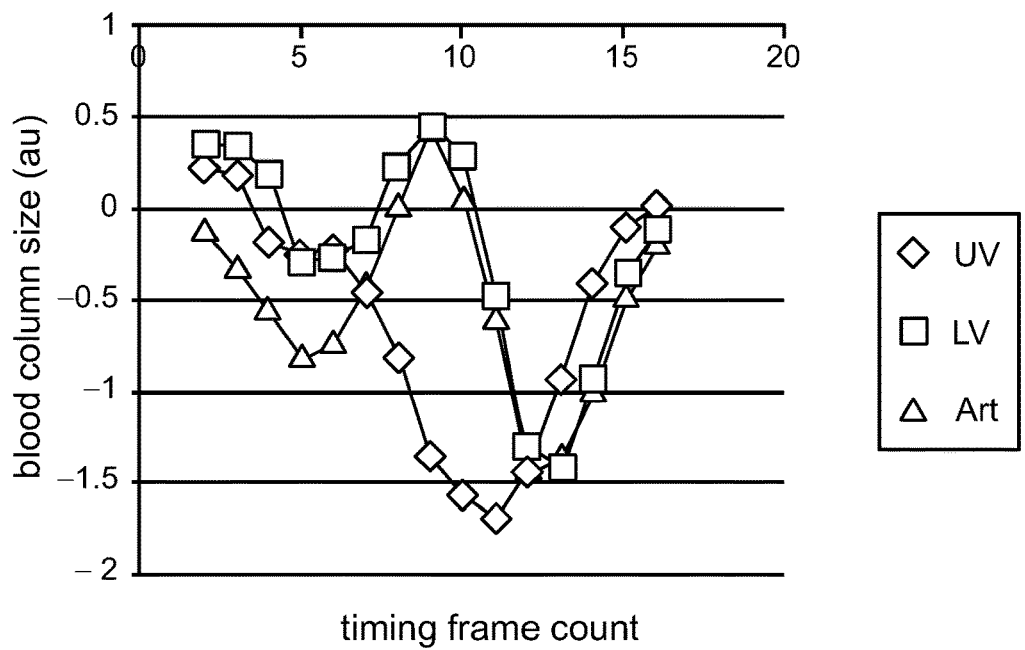
FIG. 7C is a plot of an atypical vessel blood column curve containing noisy data.
Figure 7D:
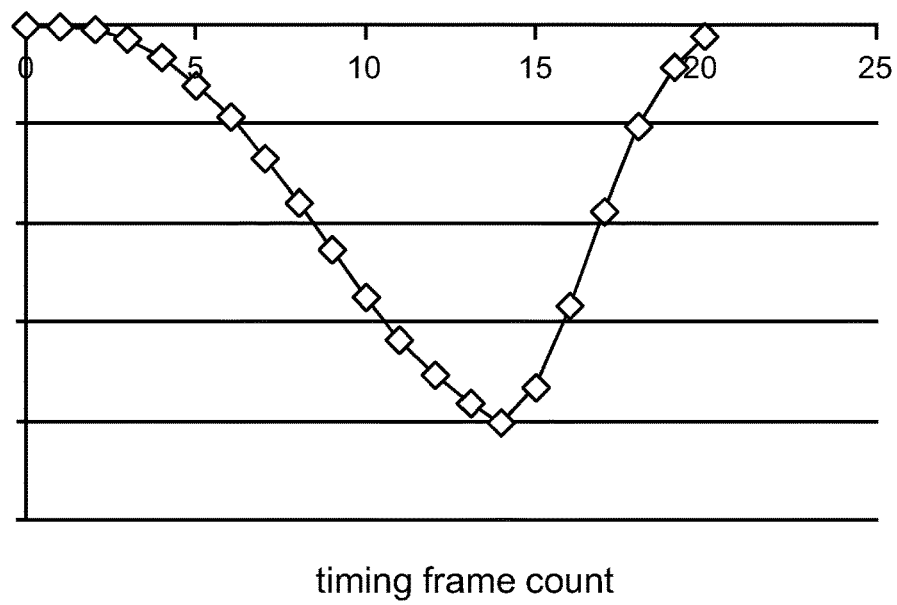
FIG. 7D is a plot of a fit to a vessel blood column curve made using capacitance discharge (down phase) and capacitance charge (up phase) incorporated into a sine-wave function referred to as a "capacitance model"

FIGS. 7A and 7B are plots of typical vessel blood column curves over a cardiac cycle, while FIG. 7C is a plot of an atypical vessel blood column curve containing noisy data. The timing is in frames (25 fps) and starts from the pulse oximeter signal near peak systole. This timing start difference is the reason for the curve variation with FIG. 6. Arterial phase data can be used as well as the two major hemivein data. Here, the amplitude and slope are calculated for the upper hemivein. Art to vein max is the time between arterial systole and venous systole. UV stands for upper hemivein, LV for lower hemivein and Art for Artery. The curves can be more accurately fitted (as shown in FIG. 7D) using capacitance discharge (down phase) and capacitance charge (up phase) incorporated into a sine-wave function and the key parameters used in subsequent analysis.

Figure 8B:
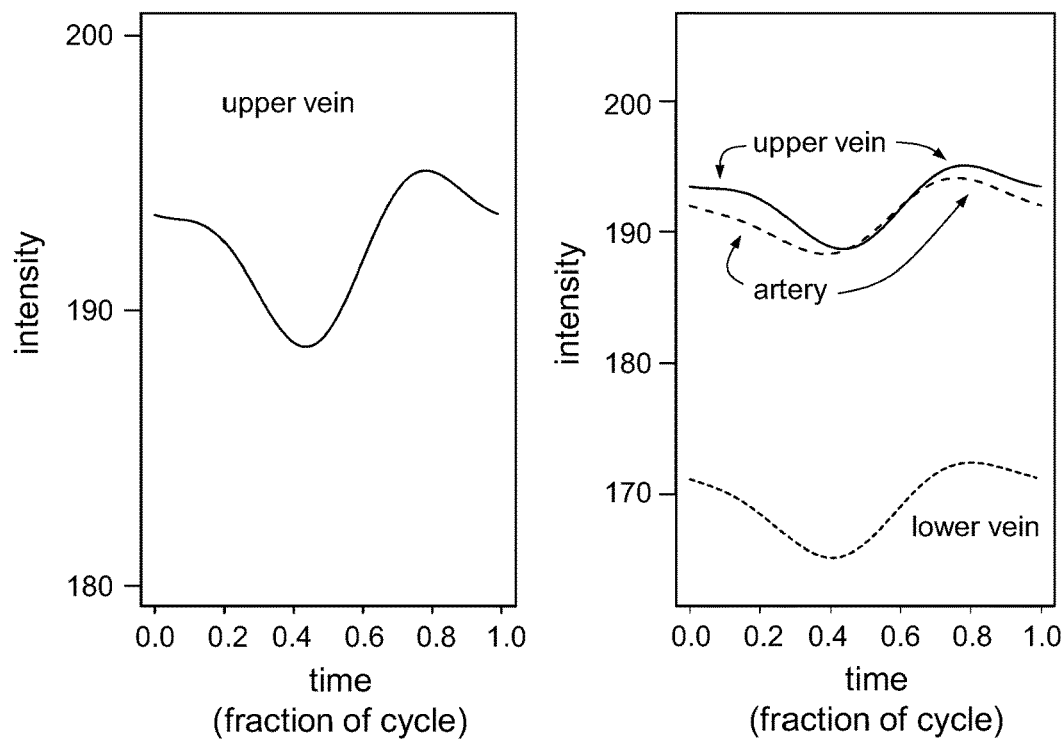
FIG. 8B are plots of the periodic components of the hemivein and artery data of FIG. 8A.

FIG. 8A is a curve fitted over three cardiac cycles of data using a Fourier two frequency model on lower hemivein data. The dichrotic notch has been extracted with this technique and its timing difference between arterial and venous segments can be compared and used similarly to the timing differences between the maxima. The periodic components of the hemivein and artery data were extracted, as shown in the right register of FIG. 8B, from which slopes, amplitudes and timing differences were calculated; in FIG. 8B, the upper vein, artery and lower vein data are shown in solid, dashed, and dotted curves respectively. (The left register of FIG. 8B shows the upper vein on its own.)

Figure 9:
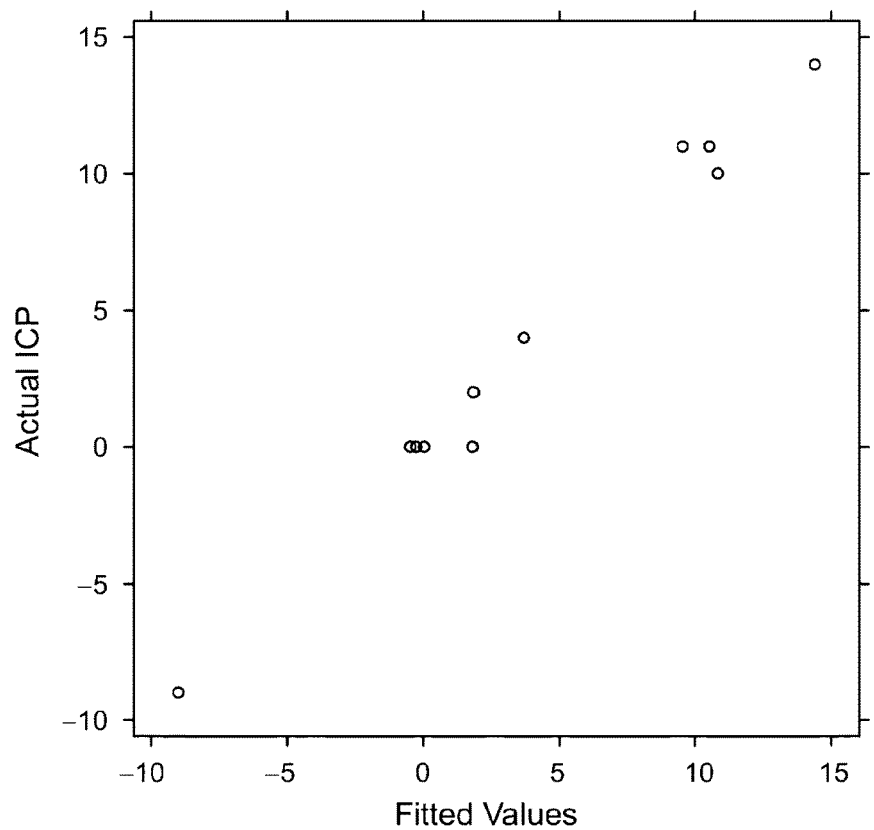
FIG. 9 is a plot of actual ICP versus the ICP results determined by the system of FIG. 1 from the key parameters.

FIG. 9 is a plot of actual ICP (measured from the EVD or ICPM from the subjects in the high dependency unit) versus the ICP results determined by system 10 from the key parameters ('lifted values'). The fitted values comprise IOP, ODF of both hemiveins, discharge rate (slope of down phase), amplitude and timing difference between artery and hemivein maxima.

Figure 10:
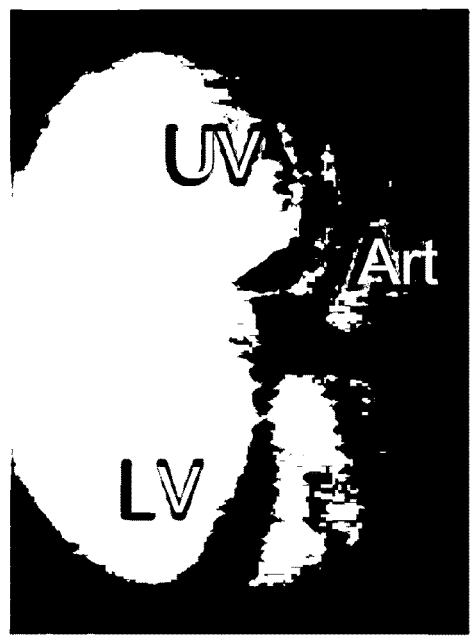
FIG. 10 is an exemplary image of an optic disk and peripapillary retina, illustrating how the optic disk may be segmented into two venous segments and one arterial segment according to an embodiment of the present invention.

FIG. 10 is an exemplary image of an optic disk and peripapillary retina, illustrating how it is segmented into two venous segments and one arterial segment according to this embodiment.

Modifications within the scope of the invention may be readily effected by those skilled in the art. It is to be understood, therefore, that this invention is not limited to the particular embodiments described by way of example hereinabove.

In the claims that follow and in the preceding description of the invention, except where the context requires otherwise owing to express language or necessary implication, the word "comprise" or variations such as "comprises" or "comprising" is used in an inclusive sense, that is, to specify the presence of the stated features but not to preclude the presence or addition of further features in various embodiments of the invention.

Further, any reference herein to prior art is not intended to imply that such prior art forms or formed a part of the common general knowledge in any country.

The invention claimed is:

1. A method for determining intracranial pressure (ICP) of a subject, the method comprising:
    applying force to an eye of a subject using an ophthalmodynamometer force (ODF) device to produce a plurality of intraocular pressure (IOP) values within the eye of the subject, wherein the ODF device is a video ophthalmodynamometer force device comprising a camera attached to a contact lens within a force transducer ophthalmodynamometer;
    imaging, using the camera, retinal vein and arterial pulsation of the eye of the subject by obtaining a plurality of images of the retina of the eye at the plurality of IOP values over at least one cardiac cycle;
    determining, using a computer, blood column density data by analyzing the images;
    determining, using the computer, amplitudes of blood column depth pulsation as a function of intraocular pressure (IOP) from the blood column density data; and
    determining, using the computer, an intracranial pressure (ICP) of the subject using the amplitude of blood column pulsation.

2. The method according to claim 1, wherein the determining the ICP comprises using:
    the amplitudes of blood column depth pulsation and a retinal vein discharge rate; or
    the amplitudes of blood column depth pulsation and a central retinal vein discharge rate.

3. The method according to claim 1, wherein the IOP is a function of a value of the force applied to the eye.

4. The method according to claim 1, wherein the determining amplitudes of blood column depth pulsation as a function of IOP employs curve fitting to and averaging of the blood column density data.

5. The method according to claim 1, comprises:
    determining from the blood column density data a retinal vein charge (inflow) rate;
    determining the ICP using the amplitudes of blood column depth pulsation and blood column depth pulsation timing information; or
    determining the ICP using the amplitudes of blood column depth pulsation and blood column depth pulsation timing information, wherein the timing information comprises a timing difference.

6. The method according to claim 1, comprising determining the ICP using the amplitudes of blood column depth pulsation and blood column depth pulsation timing information, wherein the timing information comprises a timing difference and the timing difference is between:
    time points of venous and arterial pulse maximum values and/or between time points of venous and arterial pulse minimum values; or
    venous and arterial pulse maximum points and/or minimum points for both upper and lower hemiveins.

7. The method according to claim 1, comprising imaging retinal vein and arterial pulsation at a plurality of values of the force applied to the eye and over at least three cardiac cycles.

8. The method according to claim 1, comprising measuring a baseline intraocular pressure (IOP) of the subject with an intraocular pressure measurement device, measuring venous pulsation pressure (VPP) of the subject using an ophthalmodynamometer force (ODF) device and determining venous pulsation pressure (VPP) of the subject using the ODF device and the baseline IOP thus measured.

9. The method according to claim 1, further comprising measuring venous pulsation pressure (VPP) of a second eye of the subject with an ODF device, and:
    imaging retinal vein and arterial pulsation in the second eye at a plurality of values of a force applied to the second eye with the ODF device and over at least one cardiac cycle; or
    imaging retinal vein and arterial pulsation in the second eye at a plurality of values the force applied to the second eye with the ODF device and over at least three cardiac cycles.

10. The method according to claim 1, wherein the imaging comprises making at least one video recording.

11. The method according to claim 1, comprising determining one or more of: an absolute ICP, a change in ICP, ICP waveform, retinal venous resistance, arterial resistance, and arterial compliance.

12. The method according to claim 1, comprising measuring a baseline intraocular pressure and a baseline blood pressure, and using the baseline intraocular pressure and baseline blood pressure as measured to improve accuracy of one or more results.

13. The method according to claim 1, comprising:
    determining pulse and using a pulse timing signal for cardiac cycle timing; and/or
    inducing different levels of IOP using an ODF device; and/or
    controlling an ODF device to apply a stepwise force, and thereby induce an IOP rise above baseline from 0 mm Hg to:
        a corresponding plurality of levels; or
        a corresponding plurality of levels that includes a level of approximately 50 mmHg.

14. The method according to claim 1, wherein the camera is adapted to perform the imaging and the measuring of venous pulsation pressure (VPP).

* * * * *